(12) United States Patent
Li

(10) Patent No.: US 9,518,979 B2
(45) Date of Patent: Dec. 13, 2016

(54) ASSAY TO EVALUATE DRUG METABOLISM

(71) Applicant: Albert P Li, Columbia, MD (US)

(72) Inventor: Albert P Li, Columbia, MD (US)

( * ) Notice: Subject to any disclaimer, the term of this patent is extended or adjusted under 35 U.S.C. 154(b) by 57 days.

(21) Appl. No.: 14/615,233

(22) Filed: Feb. 5, 2015

(65) Prior Publication Data

US 2016/0231313 A1 Aug. 11, 2016

(51) Int. Cl.
*G01N 33/52* (2006.01)
*G01N 33/50* (2006.01)

(52) U.S. Cl.
CPC .................. *G01N 33/5038* (2013.01)

(58) Field of Classification Search
CPC .................................................. G01N 33/5038
USPC ........................................................... 506/10
See application file for complete search history.

*Primary Examiner* — Larry Riggs
*Assistant Examiner* — Karla Dines
(74) *Attorney, Agent, or Firm* — Koren Anderson

(57) ABSTRACT

A novel assay using plated (cultured) human hepatocytes is disclosed. In this assay, cryopreserved human hepatocytes are thawed and cultured for 4 hours to allow attachment, followed by incubation with compounds for 24 hours. After the 24 hour incubation, aliquots can be collected for quantification of the remaining parent compounds. The remaining incubated media are transferred to freshly thawed and cultured cryopreserved hepatocyte and incubated for another 24 hour period. The process can be repeated daily resulting in accumulated incubation durations of multiple days. The innovation is the use of a new culture on each day, thereby overcoming the known decrease in metabolic activity of hepatocytes with time in culture.

13 Claims, 5 Drawing Sheets

ASSAY TO EVALUATE DRUG METABOLISM

TECHNICAL FIELD

The present disclosure relates to in vitro methods of evaluating drug metabolism.

BACKGROUND

Cultured human hepatocytes are a well-established in vitro model system for studying drug metabolism and potential toxicity. Routine application of hepatocytes in metabolic stability screening of new chemical entities has led to a variety of low clearance compounds (LCC) for further drug development. These LCCs have the advantages of a favorable pharmacokinetic profile which may have more prolonged pharmacological activity in the human body. Furthermore, these LLCs may be less likely to cause drug-drug interactions.

The cell culture medium must support hepatic functionality in order to reliably predict in vivo response to various drugs. However, some functions of the cultured hepatocytes decrease by more than 50% during the first 24 hours in culture.

Short-term incubations with hepatocytes may not be effective for certain LCCs. For example, the half-life of diazepam is approximately 43±13 hours.

Thus, maintenance of hepatocyte functions in vitro for greater than 24 hours remains a challenging task. Therefore, improvements in hepatocyte culture conditions could be beneficial to the drug discovery process.

SUMMARY OF THE INVENTION

As explained above, a major drawback of the use of cultured hepatocytes for prolonged (multiple days) metabolic studies is limited by the known decrease in hepatic functions with time in culture, most notably P450 and uptake transporter expression. Disclosed here is a novel method and assay for the evaluation of LCCs.

The invention comprises sequential metabolism of a test compound for multiple days, with metabolism performed using freshly cultured hepatocytes on the day of evaluation. The use of sequential metabolism using a new hepatocyte culture overcomes the culture-duration dependent decrease in hepatic metabolism capacity of long-term cultured hepatocytes. In detail, the novel method consist of evaluating the metabolism of a test compound via cultured hepatocytes includes adding a medium with a test compound to be metabolized to a first multiwell plate each having cultured hepatocytes for a first time period. After the incubation period, the medium is collected from the multiple wells, pooled into a first container, followed by distributing the pooled medium in the first container into a second multi-well plate with freshly cultured hepatocytes for incubation for a second time period. Upon completion of the incubation, the medium from the multiple wells are pooled into a second container, and the pooled medium in the second container is distributed into a third multi-well plate with freshly cultured hepatocytes for a third incubation period. The process can continue for additional days by repeat the process of medium collection, pooling, and distribution into a new plate with freshly cultured hepatocytes. The use of freshly cultured hepatocytes on each new incubation period ensures that the test article is metabolized for each incubation with freshly plated hepatocytes. The test article therefore can be evaluated for a prolonged accumulated incubation period of multiple days with hepatocytes with full metabolic capacity.

Embodiments may include one or more of the following features. For example, the time period may be 24 hours. The cryopreserved hepatocytes may be cultured in each plate of the first multi-well plate immediately prior to the first time period or on the same day as the beginning of the experiment. Hepatocytes in the wells plate of the second multiwell plate and third multiwell plate may be cultured on the same day that the hepatocytes are to be used in the experiment.

The test compound may be a drug or chemical compound that is being evaluated for therapeutic or toxicity purposes. In one embodiment, the test compound to be metabolized is added to hepatocyte cultures prepared on each day of experiment.

A portion of the medium (aliquot) may be removed from container for analysis prior to distribution to the next multiwell plate.

DETAILED DESCRIPTION

Figure 1:
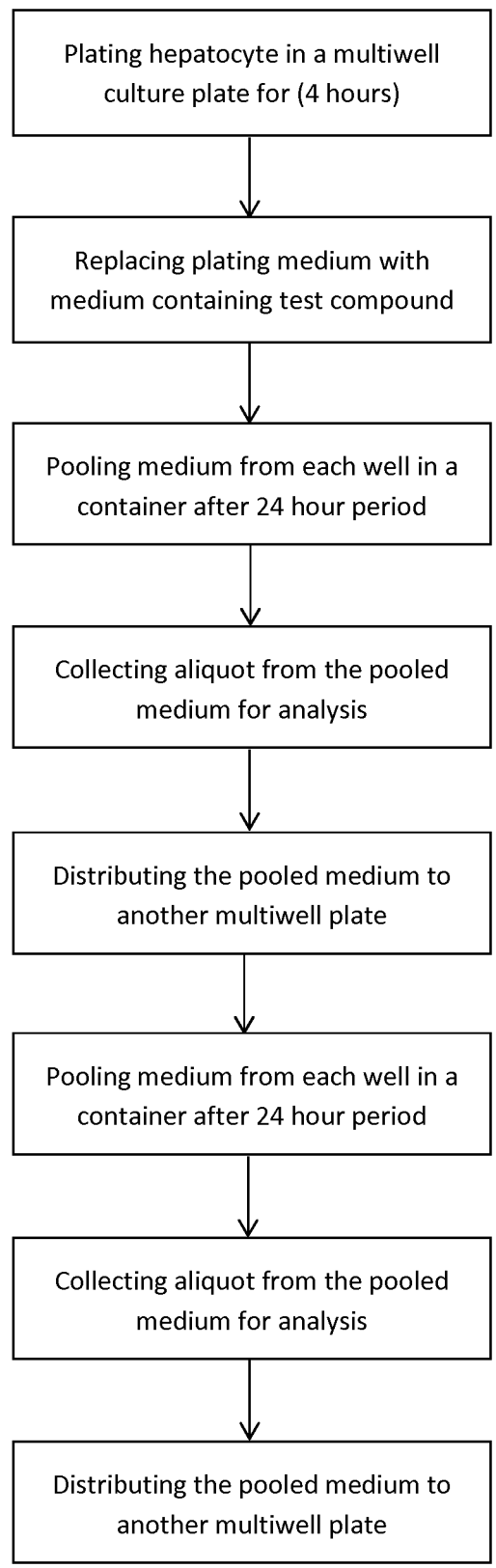
FIG. 1 illustrates an embodiment of the assay method.

Referring to FIG. 1, in operation 10 hepatocytes are plated in a multiwell culture plate and incubated for 4 hours. Plateable cryopreserved human hepatocytes can be used in this assay. The hepatocytes can be used both as single donor cultures as well as cultures of a mixture (pool) of the hepatocytes from the multiple donors.

The assay can be performed using multi-well plates, such as, 48-well or 96-well, or 1536-well cell culture plates. The hepatocytes can be plated on surfaces that ensure adhesion and confluence. The hepatocytes are cultured in an incubator maintained at 37° C. with a humidified atmosphere of 95% air and 5% carbon dioxide.

In operation 20, the plating medium is replaced with a medium containing a test compound that has been cultured on the same day of the experiment. The multiwell culture plate is incubated for a period of 24 hours. Aliquots can be removed from the media before addition to the hepatocytes to represent time 0 (no metabolism) concentrations.

After the 24 hour incubation period, the medium from each well is collected and pooled in a container in operation 30. An aliquot is collected from the pooled medium for analysis in operation 40. For example, the aliquot may be analyzed by liquid chromatography-tandem mass spectrometry (LC/MS) quantification.

Hepatocytes are cultured in a second multiwell plate on the second day of the experiment. The pooled medium from the first incubation in the container is distributed into the wells of this second multiwell plate for another 24 hour period (a second day) in operation 50. Media from each well is collected and pooled in another container in operation 60. Once again, an aliquot is collected from the pooled medium for analysis in operation 70.

Hepatocytes are cultured in a third multiwell plate on the third day of the experiment. In operation 80, the medium is distributed in the third multiwell plate for a third incubation period of 24 hours. Thus, the total incubation period with active hepatocytes may be 72 hours. However, this procedure can be repeated several more times, thereby allowing an extended total incubation period.

Figure 2:
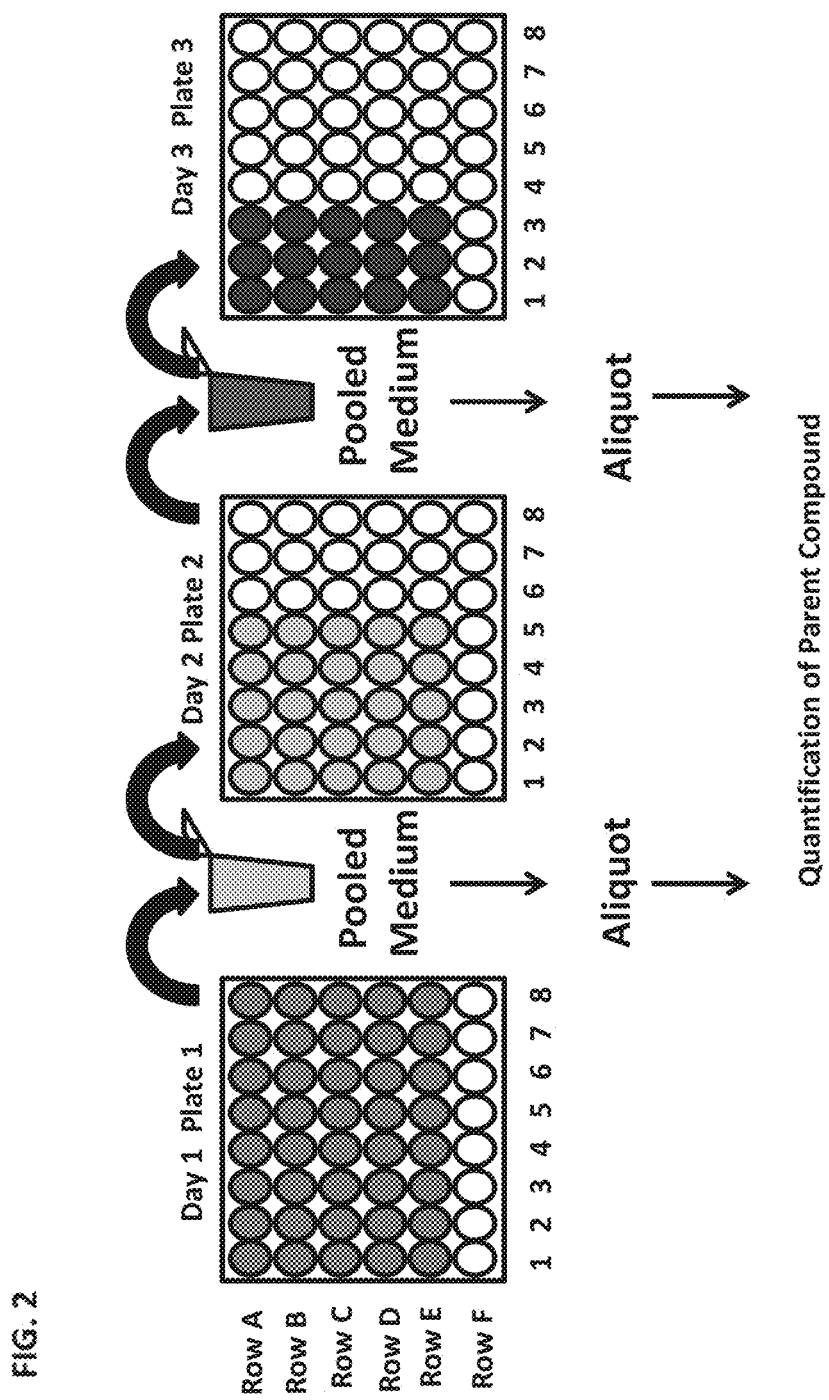
FIGS. 2-3 provide schematic views of the method using multiwell culture plates.
Figure 3:
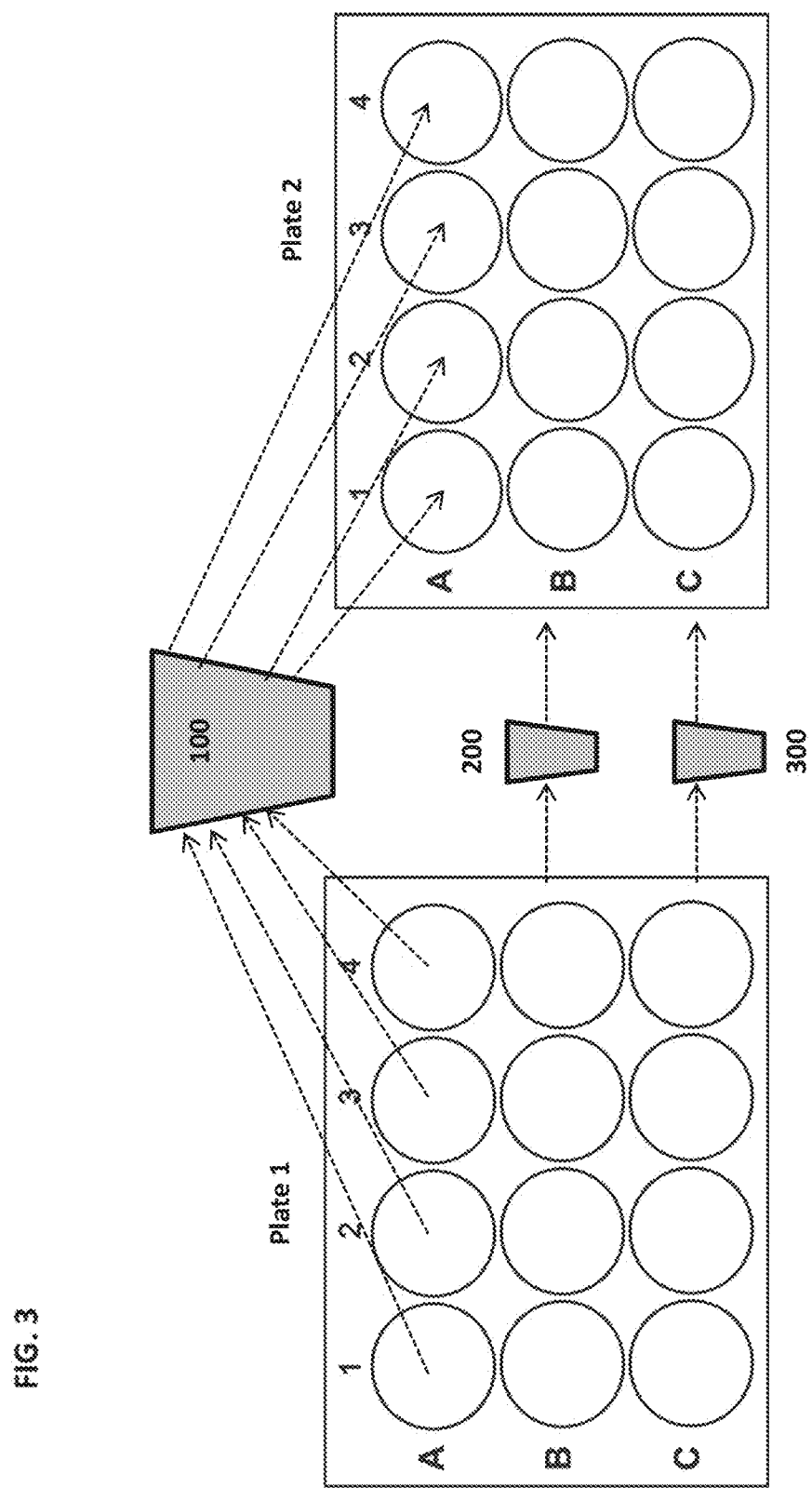

FIGS. 2 and 3 are schematic views of multiwell plates used in an embodiment of the assay method. Referring to FIG. 2, each well of rows A-E, columns 1-8 of plate 1 have cultured hepatocytes and a fluid medium that includes the test compound. The medium is pooled in a second container, as shown by the arrow, after 24 hours. An aliquot is removed from the pooled medium and the medium is then distributed to wells of rows A-E, columns 1-5 of plate 2.

The medium is pooled in a third container, as shown by the arrow, after 24 hours. An aliquot is removed from the pooled medium and the medium is then distributed to wells of rows A-E, columns 1-3 of plate 3.

Referring to FIG. 3, two multiwell plates 1, 2 are illustrated. The plates 1, 2 have three rows (A, B, C) and four columns (1, 2, 3, 4). A container 100, 200, 300 is used to collect the medium from each row (A, B, C). In this embodiment, a different test compound can be used in each row.

Figure 4:
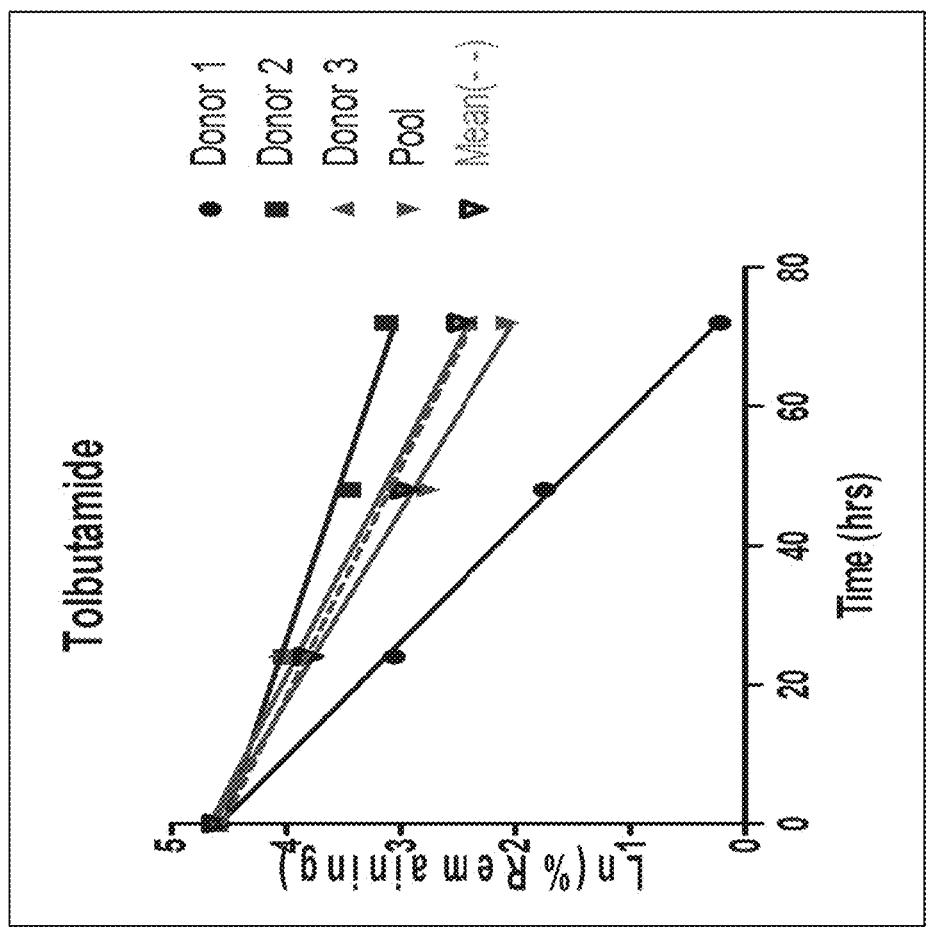
FIGS. 4-5 provide results of the assay method.
Figure 5:
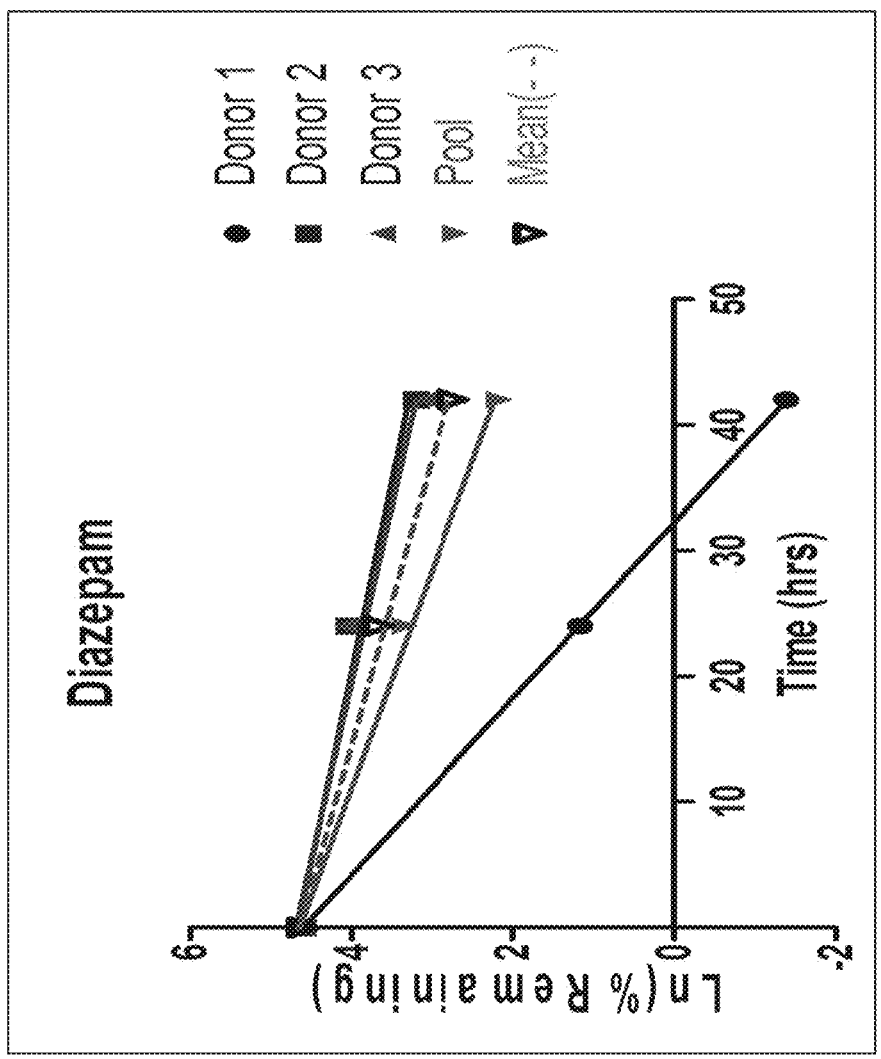

FIGS. 4 and 5 illustrated time dependent disappearance of tolbutamide and diazepam during the experiment. Natural log of the percent parent compound is plotted versus incubation time, with each incubation representing a 24 hour period. Results using single donors or pooled donors are shown. The dotted line represent mathematic mean of the percent parent compound remaining from data obtained with individual donors.

The invention claimed is:

1. A method of evaluating metabolism of a test compound via cultured hepatocytes, the method comprising:
    adding a medium with a test compound to be metabolized to a first multi-well plate each having cultured hepatocytes for a first time period;
    pooling the medium with the test compound into a first container;
    distributing the pooled medium in the first container into a second multi-well plate each having cultured hepatocytes for a second time period;
    pooling the medium with the test compound into a second container; and
    distributing the pooled medium in the second container into a third multi-well plate having cultured hepatocytes for a third time period.

2. The method of claim 1, further comprising:
    culturing cryopreserved hepatocytes in each plate of the first multi-well plate prior to the first time period.

3. The method of claim 1, further comprising:
    culturing cryopreserved hepatocytes in each plate of the second multi-well plate between the first and second time period.

4. The method of claim 1, further comprising:
    culturing cryopreserved hepatocytes in each plate of the third multi-well plate between the second and third time period.

5. The method of claim 1, where the first, second and third time period each comprise 24 hours.

6. The method of claim 1, wherein the test compound comprises a chemical compound.

7. The method of claim 1, wherein the test compound comprises a drug.

8. The method of claim 1, further comprising:
    adding the test compound to be metabolized to the medium.

9. The method of claim 1, wherein the test compound to be metabolized is added to hepatocyte cultures prepared on each day of the experiment.

10. The method of claim 1, wherein:
    the first multi-well plate includes more than one row and more than one column of wells;
    pooling the medium includes pooling the medium from each row of wells;
    distributing the pooled medium includes distributing the pooled medium to wells of a corresponding row of the second multi-well plate;
    pooling the medium with the test compound into a second container; and
    distributing the pooled medium in the second container into a third multi-well plate having cultured hepatocytes for a third time period.

11. The method of claim 1, further comprising:
    removing a portion of the medium from the first container for analysis or other treatment.

12. The method of claim 1, further comprising:
    removing a portion of the medium from the second container for analysis or other treatment.

13. A method of evaluating metabolization of a drug via cultured hepatocytes during a multi-day experiment, the method comprising:
    culturing cryopreserved hepatocytes in each plate of a first multi-well plate on a first day of the experiment;
    adding a medium with the drug to be metabolized to the first multi-well plate for the first day of the experiment;
    culturing cryopreserved hepatocytes in each plate of a second multi-well plate on a second day of the experiment;
    pooling the medium into a first container on the second day of the experiment;
    removing a portion of the medium from the first container for analysis or other treatment;
    distributing the pooled medium in the first container into the second multi-well plate for the second day of the experiment;
    culturing cryopreserved hepatocytes in each plate of a third multi-well plate on a third day of the experiment;
    pooling the medium into a second container on the third day of the experiment;
    removing a portion of the medium from the second container for analysis or other treatment; and
    distributing the pooled medium in the second container into the third multi-well plate for the third day of the experiment.

* * * * *